US008062658B2

(12) United States Patent
Shalaby et al.

(10) Patent No.: US 8,062,658 B2
(45) Date of Patent: *Nov. 22, 2011

(54) MULTICOMPONENT BIOACTIVE INTRAVAGINAL RING

(75) Inventors: Shalaby W Shalaby, Anderson, SC (US); Georgios T Hilas, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1049 days.

This patent is subject to a terminal disclaimer.

(21) Appl. No.: 11/974,140

(22) Filed: Oct. 11, 2007

(65) Prior Publication Data

US 2008/0069850 A1  Mar. 20, 2008

Related U.S. Application Data

(63) Continuation-in-part of application No. 11/667,933, filed as application No. PCT/US2005/045190 on Dec. 14, 2005.

(60) Provisional application No. 60/635,887, filed on Dec. 14, 2004.

(51) Int. Cl.
*A61F 13/15* (2006.01)
(52) U.S. Cl. .................................................. 424/433
(58) Field of Classification Search .................. None
See application file for complete search history.

(56) References Cited

U.S. PATENT DOCUMENTS

2004/0265355 A1  12/2004  Shalaby
2005/0053639 A1  3/2005  Shalaby
2005/0175664 A1  8/2005  Hunter et al.

*Primary Examiner* — Carlos Azpuru
(74) *Attorney, Agent, or Firm* — McCormick, Paulding & Huber LLP

(57) ABSTRACT

Intravaginal ring devices have multicomponent drug releasing substrates loaded with at least one bioactive agent and designed to effect contraception and/or provide means to treat and/or prevent diseases caused by infectious bacteria, fungi, virus, and retroviruses, without compromising the primary function of normally occurring, useful vaginal microflora in female patients.

28 Claims, No Drawings

MULTICOMPONENT BIOACTIVE
INTRAVAGINAL RING

This application is a continuation-in-part of U.S. Ser. No. 11/667,933, filed on May 16, 2007, and entitled "Intravaginal Ringed-mesh Device and Applicator Therefor," which was subject of a PCT Application, Ser. No. PCT/US05/45190, filed on Dec. 14, 2005, which, in-turn, claims the benefit of a prior provisional Application, Ser. No. 60/635,887, filed on Dec. 14, 2004.

FIELD OF THE INVENTION

This invention is directed to a family of bioactive intravaginal ring devices formed of at least two polymeric materials, at least one bioactive agent capable of exhibiting antibacterial, antifungal, and/or antiviral activity in the vagina and surrounding tissues of animals and humans without compromising the function of useful microflora therein. The design of the rings and concentration and release profile of the agent(s) are tailored to maximize the effective use of any specific ring system.

BACKGROUND OF THE INVENTION

Prior applications of the same inventor have dealt with a fiber-reinforced composite ring for the controlled release of at least one bioactive agent incorporated in a biocompatible matrix reinforced with absorbable/biodegradable fibers capable of providing the mechanical properties needed for inserting and maintaining the ring in a body cavity for a desired period of time. Such ring system can be used for the intravaginal, intraperitoneal, and subcutaneous delivery of at least one bioactive agent, including those used as contraceptives. More specifically, the prior applications consist of those described below.

U.S. application Ser. No. 10/860,677, hereby incorporated herein by reference in its entirety, discloses a controlled drug release device comprising a partially or fully absorbable, fiber-reinforced composite ring system comprising an absorbable or non-absorbable matrix, an absorbable, reinforcing fibrous construct and an absorbable coating to provide three modes of controlling the release of bioactive agents and one mode for modulating the mechanical property of the ring in a body cavity during device functional use. For partially absorbable ring systems, the drug release is dependent initially on the diffusion rate of the drug through the matrix and the absorbable coating. As the latter degrades with time, the diffusion through the matrix prevails. Meanwhile, as the absorbable fibrous reinforcing construct undergoes degradation with time, the mechanical strength of the composite ring decreases to provide the desired mechanical strength retention profile. For a fully absorbable composite ring system, the degradation of the matrix offers an additional mode of controlling the release profile as compared with the partially absorbable counterpart. In effect, the invention of U.S. application Ser. No. 10/860,677 deals with a fiber-reinforced composite ring system for the controlled release of at least one bioactive agent comprising a biocompatible matrix reinforced with an absorbable/biodegradable fibrous construct capable of providing the mechanical properties needed for inserting and maintaining said ring in a body cavity for the desired period of time, wherein the absorbable/biodegradable reinforcing fibers are made primarily from at least one cyclic monomer such as glycolide, l-lactide, ε-caprolactone, p-dioxanone, and trimethylene carbonate.

U.S. application Ser. No. 10/935,808 was filed on Sep. 8, 2004 as a continuation-in-part application of U.S. Ser. No. 10/860,677, described above, and dealt with a partially absorbable, fiber-reinforced composite for the controlled delivery of at least one bioactive agent. The composite included an absorbable fiber construct capable of providing time-dependent mechanical properties of a biostable elastomeric copolymeric matrix containing an absorbable microparticulate ion-exchanging polymer to modulate the release of the bioactive agent for the desired period of time at a specific biological site. In accordance with that invention (1) the absorbable reinforcing fibers were formed from at least one cyclic monomer selected from glycolide, l-lactide, ε-caprolactone, p-dioxanone, trimethylene carbonate, and a morpholine-2,5-dione; and (2) the biostable matrix was made of a polyether urethane elastomer or a silicone elastomer, such as a copolymer polysiloxane, including dimethyl siloxane sequences, which can be one of the Silastic® family of silicone elastomers.

Obviously, applications Ser. Nos. 10/860,677 and 10/935,808 and related teachings did not disclose (1) the use of a non-absorbable reinforcing construct in the composite ring; (2) a novel cross-sectional geometry of the ring and associated clinical benefits in terms of ease of placement and minimized vaginal tissue trauma; (3) use of a novel feature entailing the presence of a mesh encircled by the composite ring, wherein such mesh can be used as a spermiostatic net in a contraceptive device and/or a depot for the release of bioactive agents including antimicrobials and antivirals; and (4) a ring applicator that can be used as needed by the patient without physician intervention. This led to a series of related applications, namely U.S. provisional application No. 60/635,887, filed on Dec. 14, 2004, PCT application No. US05/45190, filed on Dec. 14, 2005, and U.S. Application Ser. No. 11/667,933, filed on May 16, 2007, hereby incorporated herein by reference in its entirety.

U.S. application Ser. No. 11/667,933 is directed in general to an intravaginal device which is a ringed, flat mesh encircled with a fiber-reinforced composite ring, the composite ring providing for the controlled delivery of at least one bioactive agent, the ring being formed of a fibrous construct contained within a compliant, elastomeric copolymeric matrix, the fibrous construct providing adequate stiffness and resilience for in-use biomechanical stability, the copolymeric matrix further containing solid excipients to modulate the pH about the ring and the concentration of the at least one bioactive agent. More specifically, this case is directed to an intravaginal device comprising a ringed, flat mesh encircled with a fiber-reinforced composite ring for the controlled delivery of at least one bioactive agent. The ring is a fibrous construct that is capable of imparting needed stiffness, resilience, and in-use biomechanical stability to the compliant elastomeric copolymeric matrix thereof containing solid excipients to modulate the pH of the aqueous eluates and concentration of the bioactive agent or agents released therein. The mesh is a biostable, non-woven, melt-blown, porous polyolefin fabric, such as those made of polyethylene or polypropylene, having an average pore diameter of less than 100 microns and preferably less than 20 microns and more preferably less than 7 microns and the encircling ring is made of a crosslinked silicone elastomeric copolymer reinforced with a circular band of high-melting multifilament yarn sized with a low-melting polymer. In a specific situation, the flat fabric mesh is made of melt-blown fabric comprising polypropylene microdenier fibers and the fiber-reinforced composite ring is a crosslinked silicone elastomer reinforced with polyethylene terephthalate multifilament band sized with poly-ε-caprolactone wherein the matrix contains ferrous gluconate or ferrous ascorbate as a spermiostatic/spermicidal agent and at least one excipient selected from the group represented by ascorbic acid, carboxyl-bearing polyglycolide, glycine, citric acid, oxalic acid, tartaric acid, and glycolic acid. Because of its composition and design, the intravaginal device is conceived as a multifaceted, biomechanically, biochemically, and pharmacologically active device for securing contraception in humans and animals. A key feature of such device and particularly the flat mesh is that the polypropylene fibers of the mesh are surface sulfonated to repel approaching, negatively charged sperms. This is associated with the fact that the sperms have a negatively charged surface that will be repelled by the negatively charged sulfonate-bearing surface of the mesh. This and the limited porosity of the mesh, which can be associated with a pore diameter of less than 7 microns, will prevent the sperm diffusion through the mesh as the sperm has a head diameter of about 7 microns. Another key feature of the polyolefin or more specifically polypropylene flat mesh is that its fibers may contain an antimicrobial agent or agents such as triclosan. Obviously, these applications did not deal with certain aspects of the intravaginal ring system which include the use of surface-activated, knitted, ringed-mesh having an average pore diameter exceeding 100 micron—this is well beyond an order-of-magnitude difference from the sperm head diameter of about 7 micron and higher than the previously disclosed mesh pore diameter described as being less than 100 micron.

In spite of the broad scope of the different patent applications discussed above, there have been no specific aspects dealing with (1) improving, distinctly, the composition of the polymeric matrix of the rings, disclosed earlier, to tailor their clinical use and increase their commercial significance as intravaginal, bioactive rings, which can be economically manufactured without compromising their clinical efficacy—this is most relevant to the ringed-mesh of U.S. application Ser. No. 11/667,933 and its multifunctional use for the bimodal release of contraceptive agent(s) as well as one or more bioactive agent(s), selected from among those known to exhibit biocidal, microbicidal, antiviral, and particularly, anti-retroviral activities; (2) delimiting the silicone-based ring system to the fiber-reinforced form and addressing the application of novel coating when used for the controlled release of bioactive agents other than those disclosed earlier to exhibit contraception—this is most relevant to the use of coated, unreinforced, silicone-based, intravaginal ring for the controlled release of highly potent bioactive agents selected from among those known to exhibit biocidal, microbicidal, antiviral, and particularly, antiretroviral activities; (3) using unique combinations of hydrophilic and hydrophobic polymers to produce intravaginal ring systems with or without novel coating to achieve single-mode and bimodal controlled release of bioactive agents selected from among those known for their biocidal, microbicidal, antiviral and particularly, antiretroviral activities; and (4) providing antiretroviral intravaginal delivery systems for the prevention and treatment of human immunodeficiency virus (HIV) using traditional drugs as well as other drugs that are not known for their antiretroviral activities. Acknowledgment of the deficiencies of the earlier applications filed by the present inventor provided a strong incentive to pursue the present invention and address such deficiencies.

SUMMARY OF THE INVENTION

Thus, in a major aspect of the present invention is directed to a multicomponent microbicidal contraceptive intravaginal ringed-mesh device which is a ringed-mesh construct of a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate for the independent controlled release of at least one contraceptive agent and at least one bioactive agent, wherein the ring matrix is silicone and the fibrous mesh is polyester, and wherein the ring matrix contains at least one contraceptive agent and the polymeric coating contains at least one bioactive agent.

A specific aspect of the invention deals with a multicomponent microbicidal contraceptive intravaginal ringed-mesh device comprising a ringed-mesh construct comprising a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate for the independent controlled release of at least one contraceptive agent and at least one bioactive agent, and wherein the fibrous mesh comprises an absorbable knitted mesh having an average pore diameter of more than about 100 micron, wherein the ring contains at least one non-hormonal spermiostatic/spermicidal agent, and wherein the polymeric coating comprises at least one potent bioactive agent selected from the group consisting of metronidazole, miconazole, penciclovir, acyclovir, a combination of zidovudine and lamivudine, mitomycin, 5-flurouracil, leflunamide, enfuvirtide, gemcitabine, and paclitaxel.

A key aspect of the present invention describes a multicomponent microbicidal contraceptive intravaginal ringed-mesh device comprising a ringed-mesh construct comprising a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate for the independent controlled release of at least one contraceptive agent and at least one bioactive agent, wherein the ring matrix contains at least one contraceptive agent and wherein the polymeric coating contains at least one bioactive agent, and wherein the ring matrix contains microparticulates of ferrous gluconate, ascorbic acid, glycine, and polyglycolic acid and wherein the polymeric coating contains at least one bioactive agent selected from the group consisting of antibacterial agents, antifungal agents, antiviral agents, antiretroviral agents, antineoplastic agents, anti-inflammatory agents. Meanwhile, the at least one bioactive agent is selected from the group consisting of metronidazole, miconazole, ciprofloxacin, tetracycline, ketoconazole, doxycycline, zidovudine, acyclovir, penciclovir, ganciclovir, cidofovir, lamivudine, zalcitabine, valacyclovir, stavudine, ritonavir, indinavir, didanosine, dideoxyadinosine, clotrimazole, terbinafine, chlorhexidine, mafenide, clindamycin, paclitaxel, mitomycin, 5-flurouracil, leflunamide, enfuvirtide, gemcitabine, erythromycin, ofloxacin, ceftriaxone, and cefpodoxime.

Another key aspect of this invention describes a multicomponent microbicidal contraceptive intravaginal ringed-mesh device comprising a ringed-mesh construct comprising a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate for the independent controlled release of at least one contraceptive agent and at least one bioactive agent, wherein the ring matrix contains at least one contraceptive agent and wherein the polymeric coating contains at least one bioactive agent, and wherein the polymeric coating comprises hydrophilic polymer comprising a polyethylene glycol, and a relatively hydrophobic polymer comprising an absorbable, polyaxial copolyester.

A special aspect of the invention describes a multicomponent microbicidal contraceptive intravaginal ringed-mesh device comprising a ringed-mesh construct comprising a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate for the independent controlled release of at least one contraceptive agent and at least one bioactive agent. Meanwhile, the ring matrix comprises silicone and the fibrous mesh comprises polyester, wherein the polyester fibrous mesh is chemically treated to create a polyanionic surface for repelling negatively charged sperms and immobilizing cationic bioactive agents.

Another special aspect of this invention deals with a multicomponent microbicidal contraceptive intravaginal ringed-mesh device comprising a ringed-mesh construct comprising a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate for the independent controlled release of at least one contraceptive agent and at least one bioactive agent, and wherein the ring matrix contains at least one contraceptive agent, and the polymeric coating contains at least one bioactive agent. Meanwhile, the ring matrix contains microparticulates of ferrous gluconate, ascorbic acid, glycine, and polyglycolic acid and the polymeric coating contains at least one bioactive agent selected from the group consisting of antibacterial agents, antifungal agents, antiviral agents, antiretroviral agents, antineoplastic agents, anti-inflammatory agents, while the polymeric coating contains at least one antiretroviral agent and at least one other bioactive agent, the antiretroviral agent having potentiated or aided activity induced by the at least one other bioactive agent. Furthermore, at least one other bioactive agent is selected from the group consisting of metronidazole, clindamycin, gentamicin, neomycin, tetracycline, mitomycin, 5-flurouracil, leflunamide, enfuvirtide, gemcitabine, paclitaxel, miconazole, clotrimazole, a chlorhexine salt, and mafenide.

A clinically important aspect of this invention describes a multicomponent microbicidal contraceptive intravaginal ringed-mesh device comprising a ringed-mesh construct comprising a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate for the independent controlled release of at least one contraceptive agent and at least one bioactive agent, and wherein the ring matrix contains at least one contraceptive agent and the polymeric coating contains at least one bioactive agent. Meanwhile, the ring matrix contains microparticulates of ferrous gluconate, ascorbic acid, glycine, and polyglycolic acid and wherein the polymeric coating contains at least one bioactive agent selected from the group consisting of antibacterial agents, antifungal agents, antiviral agents, antiretroviral agents, antineoplastic agents, anti-inflammatory agents, while the polymeric coating contains at least one antiretroviral agent selected from the group consisting of zidovudine, lamivudine, enfuvirtide, and gemcitabine, and at least other bioactive agent, the antiretroviral agent having potentiated or aided activity induced by the at least one other bioactive agent. Furthermore, the at least one other bioactive agent is selected from the group consisting of metronidazole, miconazole, clotrimazole, mafenide, a chlorhexidine salt, tetracycline, neomycin, mitomycin, gemcitabine, gentamicin, and clindamycin.

A pharmaceutically important aspect of this invention deals with a multicomponent microbicidal contraceptive intravaginal ringed-mesh device comprising a ringed-mesh construct comprising a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate for the independent controlled release of at least one contraceptive agent and at least one bioactive agent, and wherein the at least one bioactive agent is selected from the group consisting of metronidazole, miconazole, ciprofloxacin, tetracycline, ketoconazole, doxycycline, zidovudine, acyclovir, penciclovir, ganciclovir, cidofovir, lamivudine, zalcitabine, valacyclovir, stavudine, ritonavir, indinavir, didanosine, dideoxyadinosine, paclitaxel, mitomycin, 5-flurouracil, leflunamide, enfuvirtide, clotrimazole, terbinafine, chlorhexidine, mafenide, clindamycin, gemcitabine, erythromycin, ofloxacin, ceftriaxone, and cefpodoxime.

A technologically important aspect of this invention deals with a process for making a multicomponent microbicidal contraceptive intravaginal ringed-mesh device comprising the steps of: forming a polymeric, fibrous mesh, adjoining a reinforcing yarn about the periphery of the fibrous mesh, forming a polymeric ring matrix comprising at least one contraceptive agent onto the reinforced fibrous mesh, thereby encasing the reinforcing yarn and the mesh periphery, and applying at least one bioactive agent to the ringed-mesh, wherein the step of applying at least one bioactive agent to the ringed-mesh comprises immersing the ringed-mesh into a solution of at least one bioactive agent in an organic solvent capable of swelling the ringed-mesh and drying the ringed-mesh, thereby deswelling the ringed-mesh, such that the at least one bioactive agent is absorbed onto the surface of the ringed-mesh. Meanwhile, the resulting treated ringed-mesh is subjected to a second process comprising the step of coating the ringed-mesh with at least one polymeric coating containing at least one other bioactive agent.

Another technologically important aspect of this invention describes a process for making a multicomponent microbicidal contraceptive intravaginal ringed-mesh device comprising the steps of: forming a polymeric, fibrous mesh, adjoining a reinforcing yarn about the periphery of the fibrous mesh, forming a polymeric ring matrix comprising at least one contraceptive agent onto the reinforced fibrous mesh, thereby encasing the reinforcing yarn and the mesh periphery, and applying at least one bioactive agent to the ringed-mesh, wherein the step of applying at least one bioactive agent to the ringed-mesh comprises coating the ringed-mesh with a polymeric coating containing at least one bioactive agent, and wherein the step of applying at least one bioactive agent comprises spray-coating the fibrous mesh with a polyaxial segmented polyester containing at least one bioactive agent selected from the group consisting of antibacterial agents, antifungal agents, antiviral agents, antiretroviral agents, antineoplastic agents, and anti-inflammatory agents. Additionally, prior to spray-coating the fibrous mesh, the mesh construct is chemically pretreated to introduce carboxylic groups onto the mesh's polymer main chain through a free radically initiated reaction of maleic anhydride with the mesh polymer followed by hydrolysis of the pendant anhydride groups. It is worth noting that the untreated polymeric fibrous mesh comprises a non-absorbable polyester comprising polyethylene terephthalate and wherein the spray-coating is applied using a polymer solution comprising at least one bioactive agent.

Yet another technologically important aspect of this invention deals with a process for making a multicomponent microbicidal contraceptive intravaginal ringed-mesh device comprising the steps of: forming a polymeric, fibrous mesh, adjoining a reinforcing yarn about the periphery of the fibrous mesh, forming a polymeric ring matrix comprising at least one contraceptive agent onto the reinforced fibrous mesh, thereby encasing the reinforcing yarn and the mesh periphery, and applying at least one bioactive agent to the ringed-mesh, wherein the polymeric fibrous mesh, which is constructed from polyethylene terephthalate multifilament yarn is made non-porous by heat-pressing to a thin polyester film which has been is formed by solution casting, followed by drying, the film having a thickness of more than 25 micron. Meanwhile, the film is heat-pressed directly to the fibrous mesh at a temperature exceeding 60° C. and a pressure exceeding 200 lbs. to form an adherent total barrier for sperms. Furthermore, the adherent thin polyester film contain at least one bioactive agent selected from the group consisting of spermiostatic/spermicidal agents, antibacterial agents, antifungal agents, antiviral agents, antiretroviral agents, antineoplastic agents, and anti-inflammatory agents.

Another clinically important aspect of this invention deals with a multicomponent microbicidal contraceptive intravaginal ringed-mesh device, described in the above paragraphs, is its adjunct use in preventing and treating tissue inflammation, herpes, cervical cancer, HIV and other retroviral, viral, and sexually transmitted diseases.

Another major aspect of this invention deals with a multi-component microbicidal intravaginal ring device comprising a silicone ring having a coating thereon, the coating comprising a combination of at least one hydrophilic polymer and at least one relatively hydrophobic polymer, wherein the coated ring provides for the controlled release of at least one bioactive agent, and wherein the at least one hydrophilic polymer comprises a polyethylene glycol and the at least one relatively hydrophobic polymer comprising a polyaxial copolyester made from at least two monomers selected from the group consisting of ε-caprolactone, trimethylene carbonate, glycolide, l-lactide and p-dioxanone. Meanwhile, the at least one bioactive agent is selected from the group consisting of metronidazole, clotrimazole, miconazole, mafenide, penciclovir, valacyclovir, and famciclovir.

Another pharmaceutically important aspect of the invention deals with a multicomponent microbicidal intravaginal ring device comprising a silicone ring having a coating thereon, the coating comprising a combination of at least one hydrophilic polymer and at least one relatively hydrophobic polymer, wherein the coated ring provides for the controlled release of at least one bioactive agent, and wherein at least one bioactive agent is absorbed onto the ring prior to application of the polymeric coating. Meanwhile, the at least one bioactive agents on the ring or in the coating is selected from the group consisting of metronidazole, miconazole, ciprofloxacin, tetracycline, ketoconazole, doxycycline, zidovudine, acyclovir, paclitaxel, mitomycin, 5-flurouracil, leflunamide, enfuvirtide, gemcitabine, penciclovir, ganciclovir, cidofovir, lamivudine, zalcitabine, valacyclovir, stavudine, ritonavir, indinavir, didanosine, dideoxyinosine, clotrimazole, terbinafine, chlorhexidine, mafenide, clindamycin, erythromycin, ofloxacin, ceftriaxone, cefpodoxime, an anti-inflammatory drug, and an antineoplastic drug, such that the ring device is capable of multimodal drug release. And such device is useful for preventing and treating tissue inflammation, cervical cancer, herpes, and sexually transmitted disease in humans and animals.

Yet another major aspect of this invention addresses a multicomponent microbicidal intravaginal ring device comprising a polymeric ring, the polymeric ring comprising at least one drug releasing polymeric substrate containing at least one bioactive agent, the device having at least two drug-releasing polymeric substrates for releasing at least one bioactive agent selected from the group consisting of metronidazole, miconazole, ciprofloxacin, tetracycline, ketoconazole, doxycycline, zidovudine, acyclovir, penciclovir, ganciclovir, cidofovir, lamivudine, zalcitabine, valacyclovir, stavudine, ritonavir, indinavir, didanosine, dideoxyadinosine, clotrimazole, terbinafine, chlorhexidine, mafenide, clindamycin, gemcitabine, erythromycin, ofloxacin, ceftriaxone, mitomycin, 5-flurouracil, leflunamide, enfuvirtide, paclitaxel, and cefpodoxime, an anti-inflammatory drug, and an antineoplastic agent, wherein the polymeric ring comprises at least one hydrophilic polymer and at least one additional relatively hydrophobic polymer, and wherein the hydrophilic polymer comprises a polyalkylene oxide and the hydrophobic polymer comprises a vinyl polymer. Additionally, the hydrophilic polymer comprises polyethylene glycol and wherein the vinyl polymer comprises ethylene vinyl acetate.

Another specific aspect of this invention deals with a multicomponent microbicidal intravaginal ring device comprising a polymeric ring, the polymeric ring comprising at least one drug releasing polymeric substrate containing at least one bioactive agent, the device having at least two drug-releasing polymeric substrates for releasing at least one bioactive agent selected from the group consisting of metronidazole, miconazole, ciprofloxacin, tetracycline, ketoconazole, doxycycline, zidovudine, acyclovir, penciclovir, ganciclovir, cidofovir, lamivudine, zalcitabine, valacyclovir, stavudine, ritonavir, indinavir, didanosine, dideoxyadinosine, clotrimazole, terbinafine, chlorhexidine, mafenide, clindamycin, gemcitabine, erythromycin, ofloxacin, ceftriaxone, mitomycin, 5-flurouracil, leflunamide, enfuvirtide, paclitaxel, and cefpodoxime, an anti-inflammatory drug, and an antineoplastic agent, wherein the polymeric ring comprises at least one hydrophilic polymer and at least one additional relatively hydrophobic polymer, and wherein the hydrophilic polymer comprises a polyalkylene oxide and the hydrophobic polymer comprises a vinyl polymer. Meanwhile, at least one bioactive agent is present as part of a polymeric coating on the ring. Furthermore, at least one bioactive agent is present in the ring matrix and is also part of a polymeric coating on the ring, wherein the polymeric coating is made of at least one polymer selected from the group consisting of an absorbable polyester, a non-absorbable polyester, an ethylene vinyl acetate copolymer, a vinyl pyrrolidone copolymer, and a polyaxial segmented copolyester.

A processing aspect of the invention deals with a multi-component microbicidal intravaginal ring device comprising a polymeric ring, the polymeric ring comprising at least one drug releasing polymeric substrate containing at least one bioactive agent, the device having at least two drug-releasing polymeric substrates for releasing at least one bioactive agent selected from the group consisting of metronidazole, miconazole, ciprofloxacin, tetracycline, ketoconazole, doxycycline, zidovudine, acyclovir, penciclovir, ganciclovir, cidofovir, lamivudine, zalcitabine, valacyclovir, stavudine, ritonavir, indinavir, didanosine, dideoxyadinosine, clotrimazole, terbinafine, chlorhexidine, mafenide, clindamycin, gemcitabine, erythromycin, ofloxacin, ceftriaxone, mitomycin, 5-flurouracil, leflunamide, enfuvirtide, paclitaxel, and cefpodoxime, an anti-inflammatory drug, and an antineoplastic agent, wherein at least one bioactive agent is introduced during the ring formation.

DETAILED DESCRIPTION OF PREFERRED EMBODIMENTS

The present invention deals with several new aspects of the intravaginal controlled delivery of bioactive agents using different forms of ring devices. One of these aspects entails the introduction of new features to the ringed-mesh device described in U.S. application Ser. No. 11/667,933 to allow its multifunctional use for the bimodal and multimodal release of contraceptive agent(s) as well as one or more bioactive agent(s) selected from among those known to exhibit biocidal, microbicidal, anti-inflammatory, antiviral, and anti-retroviral activities. Such multifunctional use is achieved through improving, distinctly, the composition of the polymeric matrix of the rings without compromising their efficacy as contraceptive devices and their commercial viability as affordable devices. Further, these new features allow for the broad-based use of such rings primarily for the controlled release of antibacterial and/or antifungal agents needed for the treatment of vaginal infection, as well as use for the controlled release of one or more combinations of anti-inflammatory agents and one or more agent selected from those known to exhibit antibacterial, antifungal, antibiotic, antiviral, antiretroviral activity, as well as those drugs which are not classified as antiviral or antiretroviral agents and yet conceived to exhibit antiviral and antiretroviral activities. The combinations of the anti-inflammatory agents, particularly the non-steroidal type, with the aforementioned bioactive agents are intended to mediate the inflammation of the vaginal and surrounding tissues associated with the use of the different types of those bioactive agents.

Another new aspect of the invention deals with the use of different coated or uncoated bimodal or multimodal rings for the controlled release of one or more antineoplastic agent in the presence or absence of an anti-inflammatory drug for the treatment or prevention of cervical and ovarian cancer, among other forms of cancer affecting the female urinogenital system. Similarly, such rings are useful in broad-based applications dealing with the controlled release of antibacterial and/or antifungal agents needed for the treatment of vaginal infections as well as infections in the neighboring urinovaginal tissues and in broad-based applications dealing with the controlled release of one or more combination of anti-inflammatory agent(s) and one or more agent(s) selected from those known to exhibit antineoplastic, antibacterial, antifungal, antibiotic, and antiretroviral activities as well as those drugs or bioactive agents, which are not classified and yet conceived to exhibit antiviral and antiretroviral activities. The combinations of the anti-inflammatory agents and particularly the non-steroidal types are intended to mediate the inflammation of the vaginal and surrounding tissue associated with the use of the different types of aforementioned bioactive agents.

A special new aspect of the invention deals with the use of coated or uncoated multicomponent intravaginal contraceptive ringed-mesh devices and other forms of coated and uncoated multicomponent intravaginal ring devices for the bimodal or multimodal release of bioactive agents for the treatment or prevention of a broad range of diseases affecting the vaginal tissues and neighboring female urinogenital tissues. Among these diseases are herpes, cervical, and ovarian cancers. Of the bioactive agents described as being effective in dealing with such diseases are several forms of antiviral and antiretroviral drugs.

Another special aspect of this invention deals with a new approach to the treatment or prevention of infection due to the human immunodeficiency virus (HIV). Using a coated or uncoated multicomponent intravaginal ringed-mesh device or multicomponent ring devices comprising silicone or non-silicone polymeric materials in the ring matrix and designed for bimodal or multimodal controlled release of (1) traditional antiviral and/or antiretroviral agents with or without an anti-inflammatory drug; (2) traditional antiviral and retroviral agents in combination with one or more microbicidal agent(s) to potentiate the antiviral or antiretroviral activities; (3) bioactive agents which are not classified as antiviral or antiretroviral agents and yet conceived by the inventors to exhibit such activities; and (4) one or more combination(s) of the unclassified drug noted in item 3 with one or more anti-inflammatory agent(s) and particularly ones belonging to the non-steroidal types.

A key aspect of this invention deals specifically with anti-HIV microbicides. The pursuit of this segment of the present invention was justified in view of the facts or postulates that (1) antiviral drugs act at specific sites within the HIV cycle and to be effective, such drugs must act by directly interfering with viral enzymatic function and eliminate the ability of HIV to mediate infection; (2) certain microbicidal agents, such as some of those disclosed in the present invention, are highly potent and are not well absorbed from the vaginal cavity in order to minimize any potential problems of drug resistance; (3) having an intravaginal controlled drug device provides prolonged drug bioavailability; (4) an intravaginal ring device would be designed to include more than one drug, which can promote the concept of synergy, an approach that has been shown to be effective in HIV therapy; (5) the use of an intravaginal microbicidal ring device would substantially reduce female sex workers' risk of acquiring HIV; and (6) the activity of the synthetic 36-aminoacid peptide enfuvirtide, which inhibits HIV type 1 fusion, would be potentiated with a potent microbicide selected from among those disclosed in the present invention. The use of the new intravaginal ringed-mesh devices for combination HIV therapy, a key clinical aspect of the present invention, is consistent with most early and recent findings associated with HIV therapy as outlined below:

(1) Epidemiologic studies suggest that sexual transmission of HIV is more likely in the presence of herpes, syphilis, and other sexually transmitted diseases (STDs).

(2) Consistent use of condoms reduces transmission of HIV by protecting exposure to semen and genital sores.

(3) Transmission of HIV requires contact with body fluids containing infected cells or plasma.

(4) HIV may be present in any fluid or exudates that contains plasma, lymphocytes, specifically blood, semen, vaginal secretions, or saliva.

Further illustrations of the present invention are provided by the following examples:

EXAMPLE 1

Preparation of a Multicomponent Contraceptive Intravaginal Ringed-Mesh Device

To prepare a contraceptive intravaginal ringed-mesh device the following steps were pursued. 1.433 g ascorbic acid, 1.917 g ferrous gluconate (FeG), 0.796 g glycine, 0.795 g poly-glycolide, and 21 mg D&C Violet #2 were mixed with 13 g of a two part biomedical-grade silicone. This mixture was injected into a ring mold preloaded with an absorbable scaffold affixed to a knitted mesh of the same material as the scaffold. The mesh and scaffold for reinforcing the ring matrix are produced from a multifilament yarn prepared from a segmented l-lactide-trimethylene carbonate copolymer made according to the teaching of U.S. Pat. No. 7,192,437, incorporated herein by reference in its entirety, and patent application Ser. No. 11/820,849 (2007). The ring mold cavity was constructed to produce a ring with an outer diameter of 40 mm, and a thickness of 5 mm. Once injected, the mold was placed in an 80° C. oven for 4 hours to cure.

Using the aforementioned process, the resultant ring weighed 5.6211 g, comprising 536 mg FeG and 401 mg ascorbic acid.

EXAMPLE 2

FeG Release from a Multicomponent Contraceptive Intravaginal Ringed-Mesh Device

To study the release profile of FeG from the multicomponent contraceptive intravaginal ringed-meshed device produced in Example 1, the ring was incubated at 37° C. in 50 mL of simulated vaginal fluid (SVF). At each time period tested, the eluent was collected and fresh SVF was added. A ferrous gluconate assay was performed on the eluents to determine the amount of FeG released and the results can be seen below in Table I.

TABLE I

Ferrous Gluconate Release from a Contraceptive Intravaginal Ringed-Mesh Device.

| Day | Release of Ferrous Gluconate (mg) |
|---|---|
| 1 | 14.21 |
| 3 | 9.47 |
| 6 | 10.09 |
| 8 | 9.87 |
| 10 | 14.83 |
| 13 | 25.96 |
| 15 | 17.78 |
| 17 | 19.30 |
| 20 | 26.40 |
| 22 | 16.39 |
| 24 | 15.99 |
| 27 | 20.21 |
| 29 | 12.27 |
| 31 | 11.29 |
| 35 | 17.23 |
| TOTAL | 241.29 |

EXAMPLE 3

Preparation of a Low Molecular Weight Polyaxial Segmented Polyester

A low molecular weight polyester consisting of a polyaxial copolymer was made by the copolymerization of the following monomers: L-lactide, $\epsilon$-caprolactone, trimethylene carbonate (TMC), and glycolide using a protocol similar to that described in U.S. Pat. No. 6,794,485, incorporated herein by reference in its entirety. The resultant polymer exhibited a molecular weight of about 150 kDa and a melting temperature of about 104° C.

EXAMPLE 4

Preparation of a Metronidazole-loaded Multicomponent Contraceptive Intravaginal Ringed-Mesh Device (Microbicidal Ring I)

A multicomponent contraceptive intravaginal ringed-mesh device was prepared as in Example 1. To prepare an intravaginal ringed-mesh device loaded with metronidazole the following steps were pursued. Metronidazole, 400 mg, was placed in a beaker with 20 mL of acetone and dissolved by stirring. Once the metronidazole had dissolved, one gram of a low molecular weight polyaxial polyester (as in Example 3) was added and stirred to dissolve. The contraceptive intravaginal ring-mesh device mentioned above was then dipped into this solution for approximately five seconds, after which the ring was placed on a piece of release paper. The acetone was removed by evaporation at 25° C. under a fume hood followed by reduced pressure.

Using the aforementioned process, the resultant coated ring gained 43.6 mg, comprising 12.4 mg metronidazole and 31.2 mg low molecular weight polyaxial polyester.

EXAMPLE 5

Bacterial Inhibition from a Metronidazole-loaded Multicomponent Contraceptive Intravaginal Ringed-Mesh Device (Microbicidal Ring I)

To study the inhibition of *V. parvula* (target anaerobic bacteria), the ring from Example 4 was incubated in clostridial broth that had been inoculated with *V. parvula*. Testing was conducted at 37° C. in an anaerobic environment. After incubation (16-18 hours), optical densities were read on the spectophotometer at a wavelength of 600 nm and fresh inoculated broth was added to the ring. Percent inhibition of the ring was determined by comparing the optical density of the ring broth to the control tube's optical density. Bacterial inhibition was observed over a five-day period and pertinent data are summarized in Table II.

TABLE II

Percent Inhibition of *V. Parvula** by Microbicidal Contraceptive Ringed-Mesh Device.

| Day | Percent Inhibition |
|---|---|
| 1 | 63.4 |
| 2 | 39.9 |
| 3 | 62.3 |
| 4 | 10.1 |
| 5 | 6.6 |

*A model micro-organism for studying bacterial inhibition

EXAMPLE 6

Preparation of a Silicone-based Metronidazole-loaded Microbicidal Intravaginal Ringed Device (Microbicidal Ring II)

To prepare a silicone-based microbicidal intravaginal ring device loaded with metronidazole the following steps were pursued. 11.403 g of a two part biomedical grade silicone were mixed with 1.139 g metronidazole and 23 mg polyglycolide particles and were injected into a single cavity. Teflon mold. The silicone was then cured at 80° C. for 4 hours.

Using the aforementioned process, the resultant ring weighed 4.515 g, comprising 4.097 g silicone, 409 mg metronidazole, and 8.3 mg poly-glycolide particles.

EXAMPLE 7

Bacterial Inhibition from a Silicone-based Metronidazole Loaded Microbicidal Intravaginal Ring Device (Microbicidal Ring II)

To study the inhibition of *V. parvula* (target anaerobic bacteria) by the ring device of Example 6, the ring was incubated at 37° C. in 50 mL PBS. At each time period tested, the eluent was collected and fresh PBS was added. Eluents were then added to the clostridial broth that had been inoculated with *V. parvula* and optical densities were read on the spectrophotometer at a wavelength of 600 nm. Percent inhibition of the ring was determined by comparing the optical density of ring eluent to the control tube's optical density. Bacterial inhibition was observed over a five-day period and pertinent data are summarized in Table III.

TABLE III

Percent Inhibition of *V. parvula*\* by a Silicone-based Metronidazole-loaded Intravaginal Ring Device

| Day | Percent Inhibition |
|---|---|
| 1 | 94.46 |
| 5 | 94.77 |
| 7 | 93.33 |
| 14 | 93.41 |
| 28 | 91.27 |

\*A model micro-organism for studying bacterial inhibition

EXAMPLE 8

Preparation of a Silicone-based Miconazole-loaded Microbicidal Intravaginal Ring Device (Microbicidal Ring III)

To prepare a silicone based intravaginal ring device loaded with miconazole nitrate the following steps were pursued. The ring body was created by mixing a two part biomedical grade silicone and injecting it into an aluminum ring mold. The silicone was then cured at 130° C. for 1 hour. The coating solution was prepared using the following procedure. Micronazole nitrate, 505.4 mg, was placed in a breaker with 15 mL of a dichloromethane (DCM):Methanol (MeOH) 4:1 solution and dissolved by stirring. Once the miconazole nitrate had dissolved, 0.8619 g of polyethylene glycol (PEG) with a molecular weight of 10000 was added and stirred to dissolve. Once the PEG had dissolved, 3.4226 g of a low molecular weight polyaxial polyester (as in Example 3) was added and shaken to dissolve. The silicone ring mentioned above was then dipped into this solution for approximately five seconds, after which the ring was placed on a Teflon rod. The acetone was moved by evaporation at 25° C. under a fume hood followed by reduced pressure.

Using the aforementioned process, the resultant coated ring weighed 4.9598 g, comprising 4.7201 g silicone, 171.3 mg low molecular weight polyaxial polyester, 43.1 mg PEG 10000, and 23.3 mg miconazole nitrate.

EXAMPLE 9

Drug Release from a Silicone-based Miconazole-loaded Microbicidal Intravaginal Ring Device (Microbicidal Ring III)

To study the release profile of miconazole from the ring device of Example 8, one quarter of the ring was cut from the ring and placed into a vial containing 3 mL water. The vial was then place into a 37° C. incubator for 24 hours after which HPLC was run to determine the amount of drug released. The ring piece was then placed in 3 mL fresh water and back into the 37° C. incubator to continue the study. Typical drug release data obtained over a period of one week are summarized in Table IV.

TABLE IV

Miconazole Release from Miconazole-loaded Intravaginal Ring.

| Day | Cumulative Percent Release |
|---|---|
| 1 | 8.61 |
| 2 | 23.69 |
| 3 | 29.70 |
| 4 | 30.36 |
| 5 | 30.36 |
| 6 | 30.65 |
| 7 | 30.65 |

EXAMPLE 10

Yeast Inhibition by a Silicone-based Miconazole-loaded Microbicidal Intravaginal Ring Device (Microbicidal Ring III)

To study the inhibition of *C. albican* (target microbe) by the ring device of Example 8, one quarter of the ring was cut from the ring and incubated in yeast mold (YM) broth that had been inoculated with *C. albican*. Testing was conducted at 37° C. After incubation (16-18 hours), optical densitied were read on the spectrophotometer at a wavelength of 600 nm. Percent inhibition of the ring was determined by comparing the optical density of ring broth to the control tube's optical density. Microbial inhibition was observed over a five-day period and pertinent data are summarized in Table V.

TABLE V

Percent Inhibition of *C. albican*\* by Miconazole-loaded Intravaginal Ring

| Day | % Inhibition |
|---|---|
| 1 | 61.55 |
| 2 | 78.70 |
| 3 | 72.75 |
| 4 | 74.05 |
| 5 | 70.25 |

\*A model microorganism for studying bacterial inhibition

EXAMPLE 11

Preparation of a Non-Silicone Based Metronidazole-loaded Microbicidal Intravaginal Ring Device (Microbicidal Ring IV)

To prepare a non-silicone based microbicidal intravaginal ring device loaded with metronidazole the following steps were pursued. Three grams of PEG with a molecular weight of 4600 was placed in a beaker and heated o 130° C. to melt. Once the PEG had melted, 302 mg of metronidazole were added and mixed thoroughly before placing back into 130° C. oven for 15 minutes. Twelve grams of ethylene vinyl acetate (EVA) was added, mixed thoroughly, and placed back in 130° C . Once the mix had melted and mixed thoroughly (~15 minutes), it was placed back in 130° C. oven. The mixing step was repeated twice more (10 minutes between mixings) before transferring material to an aluminum syringe that was preheated to 130° C. The mix was injected into an aluminum ring mold that was also preheated to 130° C. and allowed to cool to room temperature before opening. Excess flash was trimmed off of the ring.

Using the aforementioned process, the resultant ring weighed 4.067 g, comprising 3.189 g EVA, 797 mg PEG 4600, and 80 mg metronidazole. The surface of the ring was then punctured at numerous points around the total circumference three millimeters deep with an 18 gauge needle to (1) increase the surface area of the ring, and (2) increase its permeability to water, thus allowing for greater release of metronidazole.

EXAMPLE 12

Drug Release from a Non-Silicone Based Metronidazole-loaded Microbicidal Intravaginal Ring Device (Microbicidal Ring IV)

To study the release profile of metronidazole from the ring device of Example 11, one quarter of the ring and placed into a vial containing 3 mL water. The vial was then place into a 37° C. incubator for 24 hours after which HPLC was run to determine amount of drug released. The ring piece was then placed in 3 mL fresh water and back into the 37° C. incubator to continue the study. Typical drug release data obtained over a period of one week are summarized in Table VI.

TABLE VI

Metronidazole Release from a Non-Silicone-based Metronidazole-loaded Intravaginal Ring

| Day | Cumulative Percent Release |
| --- | --- |
| 1 | 18.77 |
| 2 | 24.79 |
| 3 | 29.87 |
| 4 | 35.21 |
| 5 | 38.81 |
| 6 | 43.31 |
| 7 | 47.09 |

EXAMPLE 13

Bacterial Inhibition-Silicone-based Metronidazole-loaded Microbicidal Intravaginal Ring Device (Microbicidal Ring IV)

to study the inhibition of *V. parvula* (target anaerobic bacteria) by the ring device of Example 11, one quarter of the ring was cut from the ring and incubated in clostridial broth that had been with *V. parvula*. Testing was conducted at 37° C. in an anaerobic environment. After incubation (16-18 hours), optical densities were read on the spectophotometer at a wavelength of 600 nm. Percent inhibition of the ring was determined by comparing the optical density of the ring broth to the control tube's optical density. Bacterial inhibition was observed over a five-day period and pertinent data are summarized in Table VII.

TABLE VII

% Inhibition of *V. parvula*\* by a Non-silicone based Metronidazole-loaded Intravaginal ring

| Day | Percent Inhibition |
| --- | --- |
| 1 | 90.00 |
| 2 | 75.75 |
| 3 | 18.25 |
| 4 | 29.40 |
| 5 | 26.05 |

*A model microorganism for studying bacterial inhibition

EXAMPLE 14

Preparation of a Non-silicone-based Miconazole-loaded Microbicidal Intravaginal Ring Device (Microbicidal Ring V)

To prepare a non-silicone based microbicidal intravaginal ring device loaded with miconazole the following steps were pursued. Miconazole nitrate, 600 mg, was placed in 20 mL of a 4:1 DCM:MeOH solution and stirred to dissolve. Three grams of PEG 4600 was then dissolved in the miconazole solution. The solution was then poured into a tray and placed under vacuum to remove the DCM and methanol. The remaining solid was gathered and placed in a beaker and heating at 130° C. Once the PEG/miconazole had melted, twelve grams of ethylene vinyl acetate (EVA) was added, mixed thoroughly, and placed back in a 130° C. oven. Once the mix had melted and mixed thoroughly (~15 minutes), it was placed back in a 130° C. oven. The mixing step was repeated 4x more (5 minutes between mixings) before transferring material to an aluminum syringe that was preheated to 130° C. The mix was injected into an aluminum ring mold that was also preheated to 130° C. and allowed to cool to room temperature before opening. Excess flash was trimmed off of the ring.

Using the aforementioned process, the resultant ring weighed 4.101 g, comprising 3.155 g EVA, 789 mg PEG 4600, and 158 mg miconazole nitrate. The surface of the ring was then punctured at numerous points around the total circumference three millimeters deep with an 18 gauge needle to (1) increase the surface area of the ring and (2) increase its permeability to water, thus allowing for greater release of miconazole.

EXAMPLE 15

Drug Release from a Non-silicone-based Miconazole-loaded Microbicidal Intravaginal Ring Device (Microbicidal Ring V)

To study the release profile of miconazole from the ring device of Example 14, one quarter of the ring was cut from the ring and placed into a vial containing 3 mL water. The vial was then placed into a 37° C. incubator for 24 hours after which HPLC was run to determine amount of drug released. The ring piece was then placed in 3 ml fresh water and back into 37° C. incubator to continue the study. Typical drug release data obtained over a period of one week are summarized in Table VIII.

TABLE VIII

Miconazole Release from a Non-silicone-based
Miconazole-loaded Intravaginal Ring

| Day | Cumulative Percent Release |
|---|---|
| 1 | 1.88 |
| 2 | 3.34 |
| 3 | 4.48 |
| 4 | 5.61 |
| 5 | 7.30 |
| 6 | 8.32 |
| 7 | 9.60 |

EXAMPLE 16

Yeast Inhibition of Non-silicone-based
Miconazole-loaded Microbicidal Intravaginal Ring
Device (Microbicidal Ring V)

To study the inhibition of *C. albicans* (target microbe) by the ring device of Example 14, one quarter of the ring was cut from the ring and incubated in YM Broth that had been inoculated with *C. albicans*. Testing was conducted at 37° C. After incubation (16-18 hours), optical densities were read on the spectrophotometer at a wavelength of 600 nm. Percent inhibition of the ring was determined by comparing the optical density of ring broth to the control tube's optical density. Inhibition of *C. albicans* were observed over a five-day period and pertinent data are summarized in Table VIV.

TABLE VIV

Percent Inhibition of *C. albican*\* by a Non-silicone-based
Miconazole-loaded Intravaginal Ring

| Day | Percent Inhibition |
|---|---|
| 1 | 75.7 |
| 2 | 67.8 |
| 3 | 76.9 |
| 4 | 74.6 |
| 5 | 79.6 |

\*A model microorganism for studying bacterial inhibition

EXAMPLE 17

Preparation of a Non-silicone-based
Miconazole/Metronidazole-loaded Microbicidal
Intravaginal Ring Device (Microbicidal Ring VI)

To prepare a non-silicone-based intravaginal ring device loaded with both metronidazole and miconazole the following steps were pursued. The ring was produced using the procedure found in Example 14 with the following changes: 301.2 mg of miconazole nitrate were used to produce the PEG/miconazole mixture and 302.8 mg of metronidazole were added after melting the PEG/miconazole mixture.

Using the aforementioned process, the resultant ring weighed 4.055 g, comprising 3.119 g EVA, 780 mg PEG 4600, 78 mg miconazole nitrate, and 78 mg metronidazole.

EXAMPLE 18

Drug Release from a Non-silicone-based
Miconazole/Metronidazole-loaded Microbicidal
Intravaginal Ring Device (Microbicidal Ring VI)

To study the release profile of miconazole and metronidazole from the ring device of Example 17, one quarter of the ring was cut from the ring and placed into a vial containing 3 mL water. The vial was then placed into a 37° C. incubator for 24 hours after which HPLC was run to determine amount of drug released. The ring piece was then placed in 3 mL fresh water and back into the 37° C. incubator to continue the study. Typical drug release data obtained over a period of one week are summarized in Table X.

TABLE X

Miconazole and Metronidazole Release from a Non-silicone-based
Miconazole/Metronidazole-loaded Intravaginal Ring Device

| Day | Cumulative Percent Miconazole Release | Cumulative Percent Metronidazole Release |
|---|---|---|
| 1 | 0.90 | 19.53 |
| 2 | 1.56 | 29.88 |
| 3 | 1.77 | 33.52 |
| 4 | 2.01 | 37.62 |
| 5 | 2.55 | 44.33 |
| 6 | 3.12 | 48.68 |
| 7 | 3.91 | 53.41 |

EXAMPLE 19

Yeast and Bacterial Inhibition by a
Non-silicone-based
Miconazole/Metronidazole-loaded Microbicidal
Intravaginal Ring Device (Microbicidal Ring VI)

To study the inhibition of *V. parvula* (target anaerobic bacteria) and *C. albican* by the ring device of Example 17, one quarter of the ring was cut from the ring. The ring piece was incubated in clostridial broth and YM broth that had been inoculated with *V. parvula* and *C. albican*, respectively. After incubation (16-18 hours), optical densities were read on the spectrophotometer at a wavelength of 600 nm. Percent inhibition of the ring was determined by comparing the optical density of the ring broth to the control tube's optical density. Bacterial inhibition was observed over a five-day period and pertinent data are summarized in Table XI.

TABLE XI

Percent Inhibition of *V. parvula* and *C. albican* by a Non-silicone-based
Miconazole/Metronidazole-loaded Intravaginal Ring Device

| Day | Percent Inhibition of *V. parvula*[a] | Percent Inhibition of *C. albican*[b] |
|---|---|---|
| 1 | 96.8 | 75.5 |
| 2 | 72.8 | 69.7 |
| 3 | 79.5 | 72.4 |
| 4 | 67.3 | 69.5 |
| 5 | 84.8 | 75.2 |

[a]A model for studying bacterial inhibition.
[b]A model for studying yeast inhibition Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A multicomponent microbicidal contraceptive intravaginal ringed-mesh device comprising a ringed-mesh construct comprising a ring matrix encircling a fibrous mesh adjoined thereto and held in the ring lumen and a polymeric coating covering the ringed-mesh construct, wherein each of the ring matrix and the polymeric coating comprise at least one drug-releasing polymeric substrate; and wherein the polymeric substrates of the ring matrix and coating facilitate the independent controlled release of at least one contraceptive agent and at least one bioactive agent by the device.

2. A multicomponent microbicidal contraceptive intravaginal ringed-mesh device as in claim 1 wherein the ring matrix comprises silicone and wherein the fibrous mesh comprises polyester.

3. A multicomponent microbicidal contraceptive intravaginal ringed-mesh device as in claim 2 wherein the ring matrix contains at least one contraceptive agent and wherein the polymeric coating contains at least one bioactive agent.

4. A multicomponent microbicidal contraceptive intravaginal ringed-mesh device as in claim 1 wherein the fibrous mesh comprises an absorbable knitted mesh having an average pore diameter of more than about 100 micron, wherein the ring contains at least one non-hormonal spermiostatic/spermicidal agent, and wherein the polymeric coating comprises at least one potent bioactive agent selected from the group consisting of metronidazole, micronazole, ketoconazole, fluconazole, tobramycin, rapamycin, amphotericin, 5-flurocytosine, penciclovir, acyclovir, a combination of zidovudine and lamivudine, mitomycin, 5-flurouracil, leflunomide, enfuvirtide, gemcitabine, and paclitaxel.

5. A multicomponent microbicidal contraceptive intravaginal ringed-mesh device as in claim 3 wherein the ring matrix contains microparticulates of ferrous gluconate, ascorbic acid, glycine, and polyglycolic acid and wherein the polymeric coating contains at least one bioactive agent selected from the group consisting of antibacterial agents, antifungal agents, antiviral agents, antiretroviral agents, antineoplastic agents, anti-inflammatory agents.

6. A multicomponent microbicidal contraceptive intravaginal ringed-mesh device as in claim 5 wherein the least one bioactive agent is selected from the group consisting of metronidazole, miconazole, ketoconazole, fluconazole, tobramycin, rapamycin, amphotericin, 5-flurocytosine, ciprofloxacin, tetracycline, doxycycline, zidovudine, acyclovir, penciclovir, ganciclovir, cidofovir, lamivudine, zalcitabine, valacyclovir, stavudine, ritonavir, indinavir, didanosine, dideoxyadinosine, clotrimazole, terbinafine, chlorhexidine, mafenide, clindamycin, paclitaxel, mitomycin, 5-flurouracil, leflunomide, enfuvirtide, gemcitabine erythromycin, ofloxacin, ceftriaxone, and cerpodoxime.

7. A multicomponent micobicidal contraceptive intravaginal ringed-mesh device as in claim 3 wherein the polymeric coating comprises hydrophilic polymer comprising a polyethylene glycol, and a relatively hydrophobic polymer comprising an absorbable, polyaxial copolyester.

8. A multicomponent microbicidal contraceptive intravaginal ringed-mesh device as in claim 2 wherein the polyester fibrous mesh is chemically treated to create a polyanionic surface for repelling negatively charged sperms and immobilizing cationic bioactive agents.

9. A multicomponent microbicidal contraceptive intravaginal ringed-mesh device as in claim 5 wherein the polymeric coating contains at least one antiretroviral agent and at least one other bioactive agent, the antiretroviral agent having potentiated or aided activity induced by the at least one other bioactive agent.

10. A multicomponent microbicidal contraceptive intravaginal ringed-mesh device as in claim 9 wherein the at least one other bioactive agent is selected from the group consisting of metronidazole, clindamycin, gentamicin, neomycin, tetracycline, mitomycin, 5-flurouracil, leflunomide, enfuvirtide, gemcitabine, paclitaxel, miconazole, ketoconazole, fluconazole, tobramycin, rapamycin, amphotericin, 5-flurocytosine, clotrimazole, a chlorhexine salt, and mafenide.

11. A multicomponent micobicidal contraceptive intravaginal ringed-mesh device as in claim 5 wherein the polymeric coating contains at least one antiretroviral agent selected from the group consisting of zidovudine, lamivudine, enfuvirtide, and gemcitabine, and at least one other bioactive agent, the antiretroviral agent having potentiated or aided activity induced by the at least one other bioactive agent.

12. A multicomponent microbicidal contraceptive intravaginal ringed-mesh device as in claim 11 wherein the at least one other bioactive agent is selected from the group consisting of metronidazole, miconazole, ketoconazole, fluconazole, tobramycin, rapamycin, amphotericin, 5-flurocystine, clotrimazole, mafenide, a chlorhexidine salt, tetracycline, neomycin, mitomycin, gemcitabine, gentamicin, and clindamycin.

13. A multicomponent microbicidal contraceptive intravaginal ringed-mesh device as in claim 1 wherein the at least one bioactive agent is selected from the group consisting of metronidazole, miconazole, ketoconazole, fluconazole, tobramycin, rapamycin, amphotericin, 5-flurocytosine, ciprofloxacin, tetracycline, doxycycline, zidovudine, acyclovir, penciclovir, ganciclovir, cidofovir, lamivudine, zalcitabine, valacyclovir, stavudine, ritonavir, indinavir, didanosine, dideoxyadinosine, paclitaxel, mitomycin, 5-flurouracil, leflunomide, enfuvirtide, clotrimazole, terbinafine, chlorhexidine, mafenide, clindamycin, gemcitabine, erythromycin, ofloxacin, ceftriaxone, and cefpodoxime.

14. A multicomponent microbicidal contraceptive intravaginal ringed-mesh device as in claim 1 for adjunct use in preventing and treating tissue inflammation, herpes, cervical cancer, HIV, and other retroviral, viral, and sexually transmitted diseases.

15. A multicomponent microbicidal intravaginal ring device comprising a silicone ring having a coating thereon, the coating comprising a combination of at least one hydrophilic polymer and at least one relatively hydrophobic polymer, wherein the coated ring provides for the controlled release of at least one bioactive agent.

16. A multicomponent microbicidal intravaginal ring device as in claim 15 wherein the at least one hydrophilic polymer comprises a polyethylene glycol and the at least one relatively hydrophobi polymer comprising a polyaxial copolyester made from at least two monomers selected from the group consisting of $\epsilon$-caprolactone, trimethylene carbonate, glycolide, l-lactide and p-dioxanone.

17. A multicomponent microbicidal intravaginal ring device as in claim 15 wherein the at least one bioactive agent is selected from the group consisting of metronidazole, clotrimazole, miconazole, and mafenide.

18. A multicomponent microbicidal intravaginal ring device as in claim 15 comprising at least one bioactive agent comprises more than one bioactive agent selected from the group consisting of metronidazole, miconazole, penciclovir, valacyclovir, and famciclovir.

19. A multicomponent microbicidal intravaginal ring device as in claim 15 wherein the ring comprises a silicone ring and wherein at least one bioactive agent is absorbed onto the ring prior to application of the polymeric coating, wherein at least one bioactive agents on the ring or in the coating is selected from the group consisting of metronidazole, miconazole, ketoconazole, fluconazole, tobramycin, rapamycin, amphotericin, 5-flurocytosine, ciprofloxacin, tetracycline, doxycycline, zidovudine, acyclovir, paclitaxel, mitomycin, 5-flurouracil, leflunomide, enfuvirtide, gemcitabine, penciclovir, ganciclovir, cidofovir, lamivudine, zalcitabine, valacyclovir, stavudine, ritonavir, indinavir, didanosine, dideoxyinosine, clotrimazole, terbinafine, chlorhexidine, mafenide, clindamycin, erythromycin, ofloxacin, ceftriaxone, cefpodoxime, an anti-inflammatory drug, and an antineoplastic drug, such that the ring device is capable of multimodal drug release.

20. A multicomponent microbicidal intravaginal ring device as in claim 15 for preventing and treating tissue inflammation, cervical cancer, herpes, and sexually transmitted disease in humans and animals.

21. A multicomponent microbicidal intravaginal ring device comprising a polymeric ring, the polymeric ring comprising at least one drug releasing polymeric substrate containing at least one bioactive agent, the device having at least two drug-releasing polymeric substrates for releasing at least one bioactive agent selected from the group consisting of metronidazole, miconazole, ketoconazole, fluconazole, tobramycin, rapamycin, amphotericin, 5-flurocytosine, ciprofloxacin, tetracycline, doxycycline, zidovudine, acyclovir, penciclovr, ganciclovir, cidofovir, lamivudine, zalcitabrine, valacyclovir, stavudine, ritonavir, indinavir, didanosine, dideoxyadinosine, clotrimazole, terbinafine, chlorhexidine, mafenide, clindamycin, gemcitabine, erythromycin, ofloxacin, ceftriaxone, mitomycin, leflunomide, enfuvirtide, paclitaxel, and cefpodoxime, an anti-inflammatory drug, and an antineoplastic agent.

22. A multicomponent microbicidal intravaginal ring device as in claim 21 wherein the polymeric ring comprises at least one hydrophilic polymer and at least one additional relatively hydrophobic polymer.

23. A multicomponent microbicidal intravaginal ring device as in claim 22 wherein the hydrophilic polymer comprises a polyalkylene oxide and the hydrophobic polymer comprises a vinyl polymer.

24. A multicomponent microbicidal intravaginal ring device as in claim 1 wherein the hydrophilic polymeric comprises polyethylene glycol and wherein the vinyl polymer comprises ethylene vinyl acetate.

25. A multicomponent microbicidal intravaginal ring device as in claim 22 wherein at least one bioactive agent is present as part of a polymeric coating on the ring.

26. A multicomponent microbicidal intravaginal ring device as in claim 22 wherein at least one bioactive agent is present in the ring matrix and is part of a polymeric coating on the ring.

27. A multicomponent microbicidal intravaginal ring device as in claim 26 wherein the polymeric coating is made of at least one polymer selected from the group consisting of an absorbable polyester, a non-absorbable polyester, an ethylene vinyl acetate copolymer, a vinyl pyrrolidone copolymer, and a polyaxial segmented copolyester.

28. A multicomponent microbicidal intravaginal ring device as in claim 21 wherein at least one bioactive agent is introduced during the ring formation.

* * * * *